United States Patent [19]
Harrison

[11] Patent Number: 5,298,858
[45] Date of Patent: Mar. 29, 1994

[54] METHOD AND APPARATUS FOR NON-DESTRUCTIVE TESTING OF ELECTRICALLY CONDUCTIVE MATERIALS

[75] Inventor: David J. Harrison, Farnham, England

[73] Assignee: The Secretary of State for Defence in Her Britannic Majesty's Government of the United Kingdom of Great Britain and Northern Ireland, London, England

[21] Appl. No.: 828,815
[22] PCT Filed: Jul. 13, 1990
[86] PCT No.: PCT/GB90/01082
§ 371 Date: Jan. 29, 1992
§ 102(e) Date: Jan. 29, 1992
[87] PCT Pub. No.: WO91/01496
PCT Pub. Date: Feb. 7, 1991

[30] Foreign Application Priority Data
Jul. 18, 1989 [GB] United Kingdom ............ 8916423

[51] Int. Cl.$^5$ ............ G01N 27/87; G01N 27/90; G01R 33/06
[52] U.S. Cl. ............ 324/235; 324/238; 324/262
[58] Field of Search ............ 324/225, 228, 233, 234, 324/235, 239, 240, 238

[56] References Cited

U.S. PATENT DOCUMENTS

| | | | |
|---|---|---|---|
| 3,359,495 | 12/1967 | McMaster et al. | 324/235 |
| 3,449,664 | 6/1969 | Smith | 324/235 |
| 3,450,986 | 6/1969 | Chapman et al. | 324/235 |
| 4,383,218 | 5/1983 | Hansen et al. | 324/225 |
| 4,437,062 | 3/1984 | Donnelly | 324/238 |
| 4,445,089 | 4/1984 | Harrison | 324/238 |
| 4,468,619 | 8/1984 | Recues | 324/235 X |
| 4,604,574 | 8/1986 | Posluszny et al. | 324/275 X |
| 4,819,181 | 4/1989 | Tornblom | 364/507 |
| 4,916,392 | 4/1990 | Sendeff et al. | 324/235 |

FOREIGN PATENT DOCUMENTS

| | | | |
|---|---|---|---|
| 3034426 | 3/1982 | Fed. Rep. of Germany | |
| 0756325 | 8/1980 | U.S.S.R. | 324/235 |

Primary Examiner—Gerard R. Strecker
Assistant Examiner—Warren S. Edmonds
Attorney, Agent, or Firm—Nixon & Vanderhye

[57] ABSTRACT

Eddy current based method and apparatus uses a repetitive square wave signal applied to an excitation coil and operates in a pulse echo mode by gating the detected field signal at synchronized intervals to generate one or more sequences of like gated slices obtained from respective detector positions on a circular scan path. Suitable time gating to exclude surface and near-surface reflections overcomes surface clutter and flaws are detected by examination of the sequence of slices for characteristic changes in level. Both method and apparatus have special application for crack investigations at rivet fasteners or similar, e.g. in airframes, and have ability to cope with ferrous fasteners in non-ferrous material. Excitation coil and magnetic detector are combined in a probe and the latter is driven around a circular scan path. A centering display is derived by examination of the near-surface reflection signal to determine the position and level of the peak slice level on the scan path sequence of slices.

12 Claims, 5 Drawing Sheets

METHOD AND APPARATUS FOR NON-DESTRUCTIVE TESTING OF ELECTRICALLY CONDUCTIVE MATERIALS

This invention relates to a method of non-destructive testing for the presence of flaws in electrically conductive materials and to an apparatus for the same. Both the method and apparatus are applicable to the testing of materials and structures of sites of circular symmetry and are principally though not exclusively intended for the detection of flaws under or around fasteners, such as rivets, in aircraft skins or similar structures.

The holes provided in aircraft skins and the like for the installation of rivet fasteners etc provide sites where stresses are likely to be concentrated and in consequence they are a vulnerable area for initiation of fatigue cracks. Aircraft structures typically incorporate a multitude of installed fasteners and there is need to be able to inspect these structures easily and reliably to detect small fatigue cracks arising at fastener positions before these cracks reach a size where they pose a hazard to safety or else are difficult to repair. Obviously it is desirable to undertake such inspections in situ and without removing either the surface paint (if present) or the fasteners themselves.

One established technique for the investigation of sub-surface defects in conductive materials relies upon the electromagnetic effects of eddy currents induced in the structure under test by the imposition of a time varying magnetic field. This technique can cope with surface paints and has already been applied to the investigation of flaws in aircraft structures at fastener locations. The inventor's prior UK patents GB 2028510B and GB 2078965B disclose two variants of a device which detects such flaws by detecting the change in impedance exhibited by a transducer coil by virtue of its interaction with the reaction field induced in the structure, as it is moved in steps around the circumference of a fastener. The impedance of the transducer coil is in part dependent upon the reaction field from the eddy currents in the test structure and this component may be expected to change when the normal distribution of eddy current induced in the material surrounding the fastener is disturbed by the presence of a crack. Another UK patent GB 1,113,007 discloses a device incorporating a pot core and two Hall-effect devices in a probe which is rotated around the fastener position to detect the reaction field and changes to it. All the devices disclosed in the above-mentioned patent specifications rely upon the steady state characteristics of eddy current induced by a sinusoidal excitation or the like.

One problem with prior art systems such as the inventor's own systems is that coil transducers provide a poor spatial resolution because they cover a significant area of the test structure surface at any moment. Furthermore the coils provide a response which is highly frequency dependent being proportional to the time derivative of encompassed magnetic flux. This limits the ability to use an optimum frequency from the point of view of flaw detection at depth. The worst case from the point of view of an eddy-current based system is presented by a structure comprising a non-ferrous material having ferrous fasteners. Such structures are commonplace, if not predominant, in present day aircraft and an adequate test-equipment must be able to cope with them. The ferrous fastener material dominates the magnetic field within the test structure and tends to mask eddy current signals from flaws in the surrounding material. What is more any surface feature of the fastener such as the commonplace pips dimples and identification marks present exaggerated clutter against which it is difficult to distinguish a flaw signal when the fastener is ferrous and the bonded structure is non-ferrous. No current commercial eddy-current inspection equipment known to the inventor can deal adequately with this problem, neither can the equipments disclosed in the above-mentioned prior-art patent specifications.

This invention is intended to provide a convenient and effective way of examining structures at fastener locations which can provide sensitivity and discrimination in both depth and spatial orientation even when used on non-ferrous structures having ferrous fasteners. This is achieved by the use of a pulse-echo form of eddy current inspection having novel and inventive features.

Pulse-echo eddy current inspection techniques have been known previously. In GB 1197849 there is disclosed one variety of a device using this principle. In this device a coil is used to propagate narrow magnetic field pulses into a specimen. A separate coil is used to measure the field that is reflected back. The initial pulse can be delayed by a variable amount and used to trigger a circuit which samples the reflected field at an arbitrary time delay. The coil assembly is moved over the specimen surface (presumably by hand) and the output is in the form of traces which are directly viewed by eye. This method is not disclosed in the context of the detection of flaws at fastener locations and neither the method or equipment disclosed are appropriate to such a use.

In related U.S. Pat. No. 4,271,393 and U.S. Pat. No. 4,383,218 there is disclosed a pulse-echo eddy current equipment which is intended for such use. This equipment applies current pulses having a long rise time to an excitation coil and displays the reflected field signal on a storage oscilloscope for example. Flaws are detected by comparison of the displayed signal waveform with calibration data. Such an equipment could not be expected to discriminate small flaws reliably because there are many other sources of signal variation which can not be eliminated easily in an equipment reliant on calibration data to establish the background signal level.

The present invention uses a repetitive broad-band excitation signal and a moving magnetic detector and the reflected field signal is gated at time intervals synchronised to the applied slices, one slice from within each repetition of the excitation signal cycle, to provide discrimination in terms of depth of examination, whilst the flaw reflection signals are detected by isolating variations in signal level within an individual sequence of slices corresponding to varying positions on a scan path.

The claimed method is a method of non-destructive testing an electrically conductive article for the presence of flaws by an eddy current method, comprising applying a repetitive excitation signal to a coil which is placed upon the article and which is either configured such that it has a circular footprint of magnetic field or is rotated to provide same, and moving a magnetic field detector along a circular scan path on the surface of the article and within the footprint of the magnetic field whilst examining the field signal generated by the magnetic field detector for variations in the echo component thereof consequent upon its change in position on the scan path, the magnetic field detector being a Hall-effect device or other device having good spatial resolution by virtue of a small sense area and being responsive to low frequency variations of magnetic field, wherein the method is characterised in that the method is a pulse echo method utilising a square wave excitation signal applied to the excitation coil and which is in synchronism with the motion of the magnetic field detector; and further characterised in that the output signal of the magnetic field detector is processed as follows:

i. by defining within the field signal of the magnetic field detector at least one sequence of consecutive like slices, one slice from within each period between consecutive level changes of the square wave excitation signal, by correspondingly gating said field signal for each respective sequence at set time intervals synchronised to the excitation signal, such that each respective sequence of consecutive slices registers any echoes of the excitation square wave sensed by the magnetic field detector at positions along the scan path from a depth zone within the article under test for which the aggregate signal transit times to and from the depth zone fall within the gated interval; and, ii. by measuring the signal level within each slice of each sequence thereof and comparing the measured levels of same along the respective sequence and thereby identifying any change in level from the background level predominant in the sequence of slices, such a change being consequent upon the capture of an echo from a flaw in the material of the article under test in the examined depth zone corresponding to the gated interval, and the azimuth position of a flaw being indicated by the temporal position of the change in level within the respective sequence of slices.

The slices of field signal can be so delineated in time in relation to the periods between consecutive level changes of the excitation square wave, as to define an examination zone of any required thickness or any required depth.

When surface clutter may present a problem, the examination zone will exclude a near surface zone sufficient to overcome this problem. To achieve this the field signal is so gated at set intervals of time as to define at least one respective sequence of the slices which exclude a first temporal portion of the field signal in the period between consecutive level changes of the excitation square wave, this excluded temporal portion being sufficiently extensive to preclude inclusion of echoes of the excitation square wave from the surface of the article under test, within the slices of each such sequence.

The method can be applied to examine the sub-surface structure of the article as a series of stacked layers (to any number required for adequate depth discrimination) by appropriate time delimitation of respective sequences of field signal slices zone by zone.

When the method is applied to non-destructive testing at fastener locations it is important to ensure adequate alignment of the centre point of the scan path with the centre of the fastener head, although some degree of alignment error can be accommodated by suitable signal processing. A signal indicative of any existent misalignment, which is uncluttered by echoes of the excitation square wave from any sub-surface is obtained by so timing the gating of the field signal as to define a respective sequence of slices thereof which consist solely of a first temporal portion of the period between consecutive level changes of the excitation square wave.

The claimed apparatus for use in the method as claimed includes an excitation coil, a magnetic field detector which is a Hall-effect device or a similar device having good spatial resolution by virtue of a small sense area and being responsive to low frequency variations of magnetic field, and a rotational drive means, the aforementioned all being disposed within a probe unit to be placed upon an article under test which probe unit is constructed such that the magnetic field detector is driven by the rotational drive means along a circular scan path overlying and adjacent to the article being tested, wherein the apparatus is characterised in that it comprises the following:

i. an excitation signal generator operating to energise the excitation coil with a repetitive square wave excitation signal which is in synchronism with the motion of the magnetic field detector;

ii. a field signal processor operating to process the output of the magnetic field detector, having at least one channel therein and each such comprising a switching device operating to gate the incoming field signal from the magnetic field detector at intervals in synchronism with the square wave excitation signal so as to pass a sequence of consecutive like time-delimited slices of same, one such slice from within each period between consecutive level changes of the square wave excitation signal, and an integration circuit operating to integrate the signal within each passed slice of the sequence;

iii. measurement means operating to measure, for one or each channel of the field signal processor, the integrated signal level for each slice of field signal in its respective sequence thereof; and, iv. means operating to render comparison between the measured integrated signals for each slice of field signal in a respective sequence thereof, such that variations of same from any background level are apparent.

The field signal processor may comprise any number of channels. Thus there may be only one channel with means to adjust the time limits which determine the pass band or there may be more than one channel and each such can have different preset time limits.

Preferably the apparatus incorporates a computer comprising a processor and a memory unit, the computer being configured and controlled so as to maintain synchronism between the excitation signal generator and the and the coordinated operations of the switching device in each channel of the field signal processor.

Preferably also the computer is configured and programmed such as to cause the measurement means to sample each slice in its respective sequence thereof at least once for each such slice and at points in time which are in synchronism with the excitation square wave, and such as to produce a value of same or an averaged value of same for each such slice for comparison with the value for other such slices in the same sequence.

The field signal from the magnetic detector may comprise half wave signals of alternating polarity (rather than repetitive signals of common polarity) and in order to ensure that the integrated signal level has a non-zero value some means of rectifying the field signal may be incorporated into the field signal processor. In one embodiment of the invention there is within each channel of the signal processor a phase inversion device and the respective switching device is operated under the control of the computer so as to pass gate in alternate sequence from half wave to half wave the natural signal and the phase inversed signal.

Preferably the apparatus includes a visual display unit but alternatively some other means of providing output data, such as a printed record, may be provided.

For an embodiment of the invention adapted for use at fastener positions a display indicative of any alignment error between probe and fastener may be provided. To provide the data in order to generate the display a respective channel of the signal processor (or a channel controlled so as to operate accordingly) is controlled so that the switching device pass gates only the first portion of each section of field signal between consecutive repetitions of the excitation signal and this sliced signal is integrated and sampled as described above to render comparison from slice to slice in the sequence. The pattern of the alignment error signal varies with the degree of misalignment but is characterised by a peak in level whose point in time fixes the angle of the correction vector. The signal when sliced as described is free from any distortion from sub-surface reflections and this is important in determining the angle of the correction vector. The degree of misalignment is estimated from the peak value of the signal sequence chain and realignment is made on an iterative basis.

A description of the invention is given below by way of example with reference to the drawings, of which:

Figure 1:
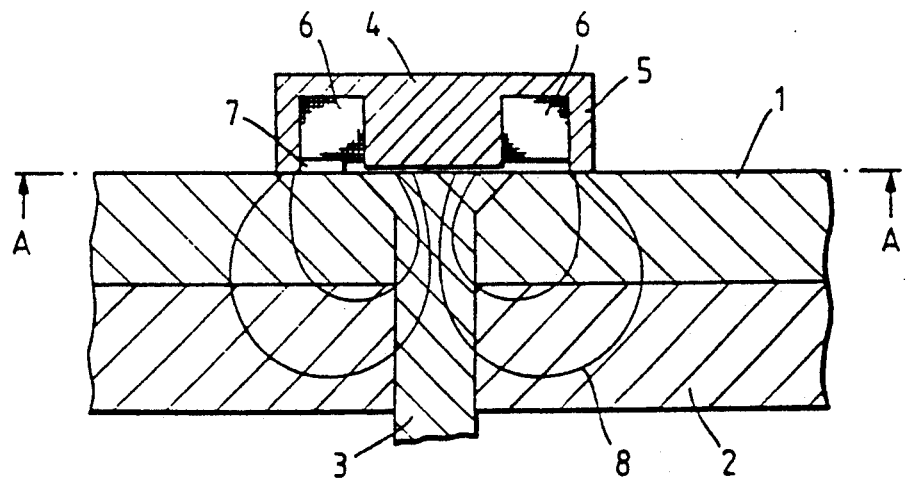
FIG. 1 is a sectional view of the electromagnetic unit.
Figure 2:
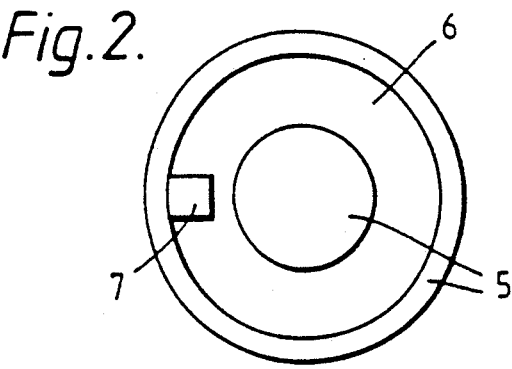
FIG. 2 is an underside view of the full electromagnetic unit on the view line AA shown in FIG. 1.

This description of an exemplary form of the equipment constituting the claimed flaw detection equipment and its operation in the manner of the claimed method is given in relation of the application thereof to the detection of cracks in an aircraft skin material or the like comprising a non-ferrous aluminium-based alloy, in the vicinity of a fastener, such as a rivet, comprising a ferrous material. In FIG. 1 the test structure is depicted as two layers of aluminium alloy, designated 1 and 2, which are joined together by a rivet fastener 3 of flush fitting countersunk form which joins the layers 1 and 2 to a support structure which is not shown. One component of the equipment is a probe (item 10 in FIG. 3) and this includes an electromagnetic unit 4 as depicted in FIGS. 1 and 2. The electromagnetic unit 4 comprises a pot core 5 of ferrite material, a circular wound excitation coil 6 and a magnetic field detector 7. These elements are all affixed to one-another to form a unitary assembly in the configuration shown.

In use of the equipment the electromagnetic unit 4 is rotated within the probe 10 with the excitation coil 6 and the magnetic detector 7 energised. The probe is placed upon the test structure such that it overlies a particular fastener and is manually adjusted to centre upon the fastener by reference to a position display system described later.

The current flowing through the excitation coil 6 establishes a magnetic field which penetrates the test structure. In the absence of any misalignment between the coil 6 and the fastener 3 and with no cracks etc present within the area this field will be circumferentially symmetric about the fastener with the field lines having the general pattern indicated at 8. In practice there is always likely to be some degree of residual misalignment which gives rise to an asymmetry within the field with respect to the centre of the electromagnetic unit 4 and this is reflected by the presence within the magnetic detector output of an alignment error which varies sinusoidally with the rotation angle of the electromagnetic unit. This alignment error component of signal can be identified and removed by signal processing.

The fastener 3 when of ferrous material has a significantly greater magnetic permeability than the surrounding aluminium alloy material and in consequence tends to act as a conduit within the test structure for the flux established therein. It has been found that there is no useful gain in performance achieved by using a magnetic core 5 having a centre limb of significantly greater or smaller diameter than the fastener head. This centre limb is sized so as to have a diameter slightly less than the typical fastener head on which it will be used. The overall diameter of the core 5 and the magnetomotive force provided by excitation coil 6 control the area of footprint and the depth of penetration. The magnetic detector 7 is so arranged as to be sensitive to that component of incident magnetic field normal to the surface of the test structure and this enables the presence of field modifying features such as flaws to be detected as a variation in level around the circular scan of the detector. In the equipment described the magnetic detector 7 is Hall effect device used because it has small physical area (providing good spatial resolution) and good low frequency response down to DC.

Figure 3:
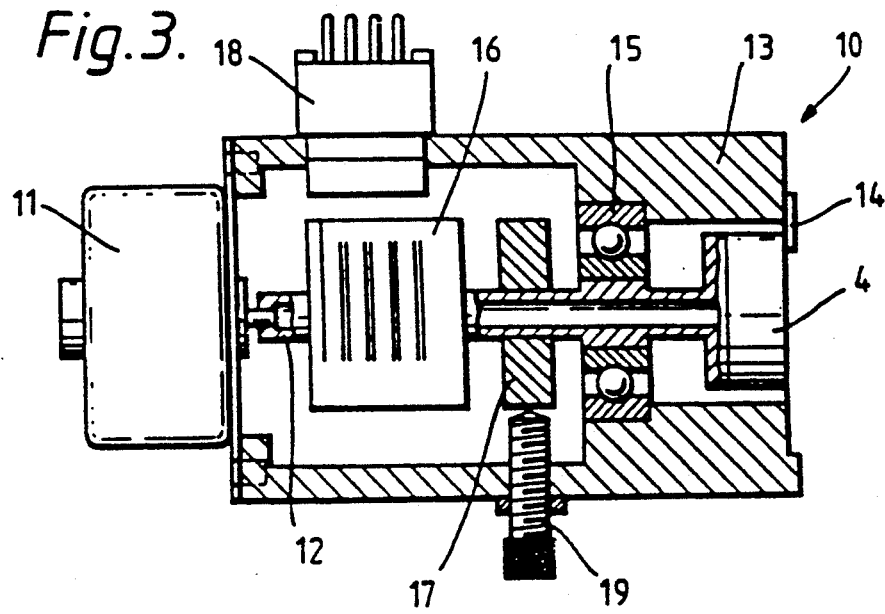
FIG. 3 is a sectional view of the workpiece probe.

FIG. 3 depicts the equipment comprising the workpiece probe generally designated 10. The electromagnetic unit 4 is driven by a stepper motor 11 the two being linked by a drive shaft 12 and being mounted upon a framework 13 of non-ferrous material. Framework 13 includes foot portions 14 by which it will bear upon the test structure (not shown in FIG. 3). The drive shaft 12 is supported by a bearing 15 and mounted upon this shaft are slip rings 16 and a ring element 17. Drive shaft 12 is hollow and electrical connections (not shown) pass from the electromagnetic unit through the drive shaft 12 and thence via the slip rings 16 to a connector 18. Ring element 17 incorporates an eccentrically mounted magnet and there is a magnetic pick-up 19 mounted upon framework 13 in a position such that it responds to the rotation of ring element 17 to produce an electrical datum pulse once per revolution of electromagnetic unit 4.

Figure 4:
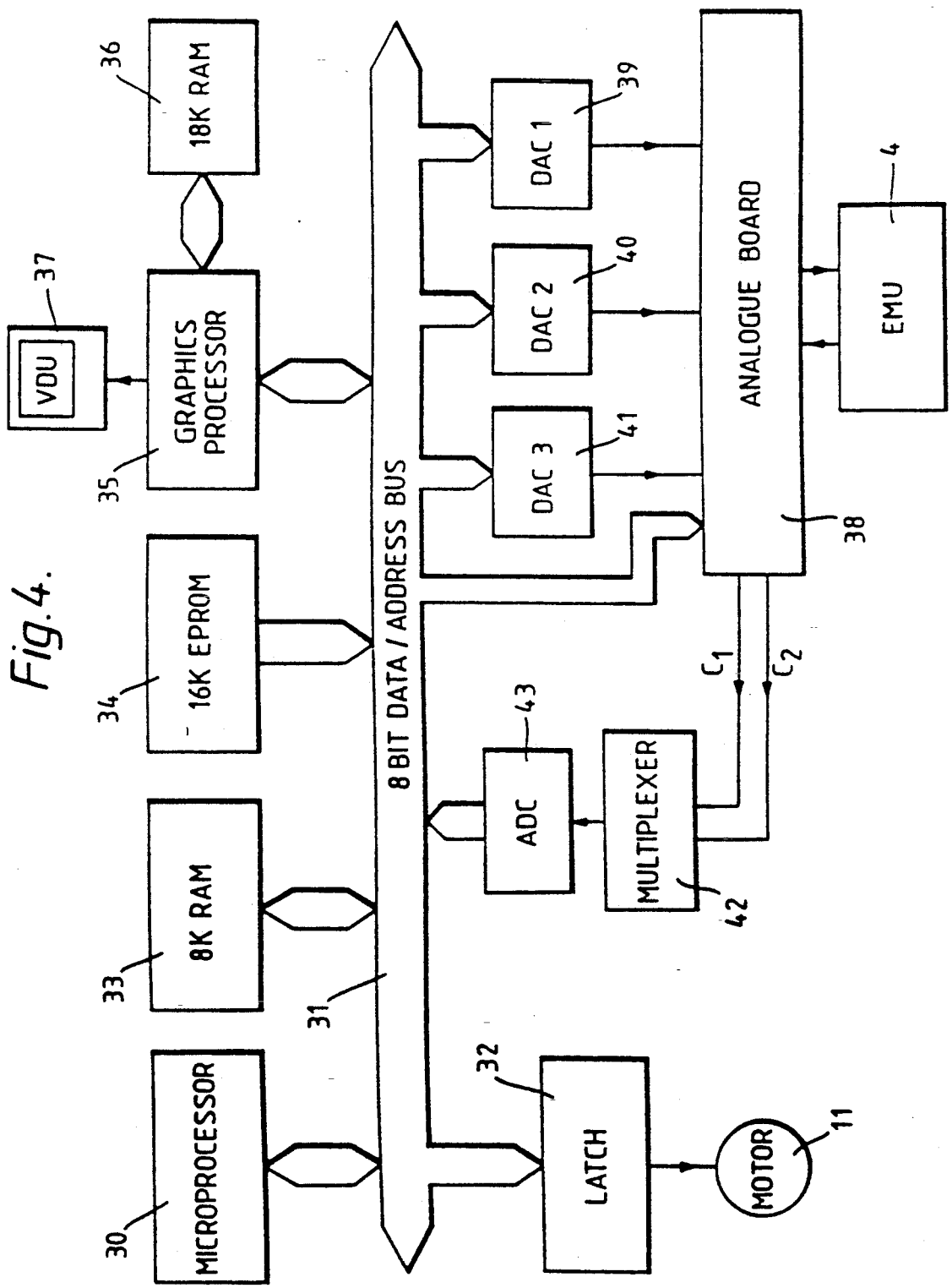
FIG. 4 is a block diagram illustrating the components of the electrical system.

FIG. 4 is a block diagram showing all the functional units of the equipment and their interrelationship. The equipment is controlled by a microprocessor 30 which communicates with other elements of the digital system via an eight bit data/address bus designated 31. A clock within the microprocessor 30 generates interrupts at 300 microsecond intervals. These are distributed via the bus 31 and serve, inter alia, to synchronise various coordinated actions. The stepper motor 11 is driven by digital commands from the bus 31 through a latch 32. Drive commands are initiated at every fourth interrupt so as to rotate the stepper motor in a progression of 200 steps per revolution and a rotational speed of approximately four revolutions per second. The microprocessor 30 has access to random access memory (RAM) 33 and to read only memory (ROM) 34. A graphics processor 35 which has independent access to a RAM 36 controls a visual display unit (VDU) 37. An analogue circuit board 38 provides an interface between the digital system and the electromagnetic unit 4. There are several channels within this circuit board 38 as explained later, two being illustrated in this Figure. A digital to analogue converter (DAC) 39 provides an input from bus 31 operative to control the excitation signal of the electromagnetic unit 4. Further DACs 40 and 41 connect with respective channels of signal processing circuitry within analogue circuit board 38. The outputs of these channels are passed through a multiplexer 42 to an analogue to digital converter (ADC) 43 and thence to the system bus 31.

Figure 5:
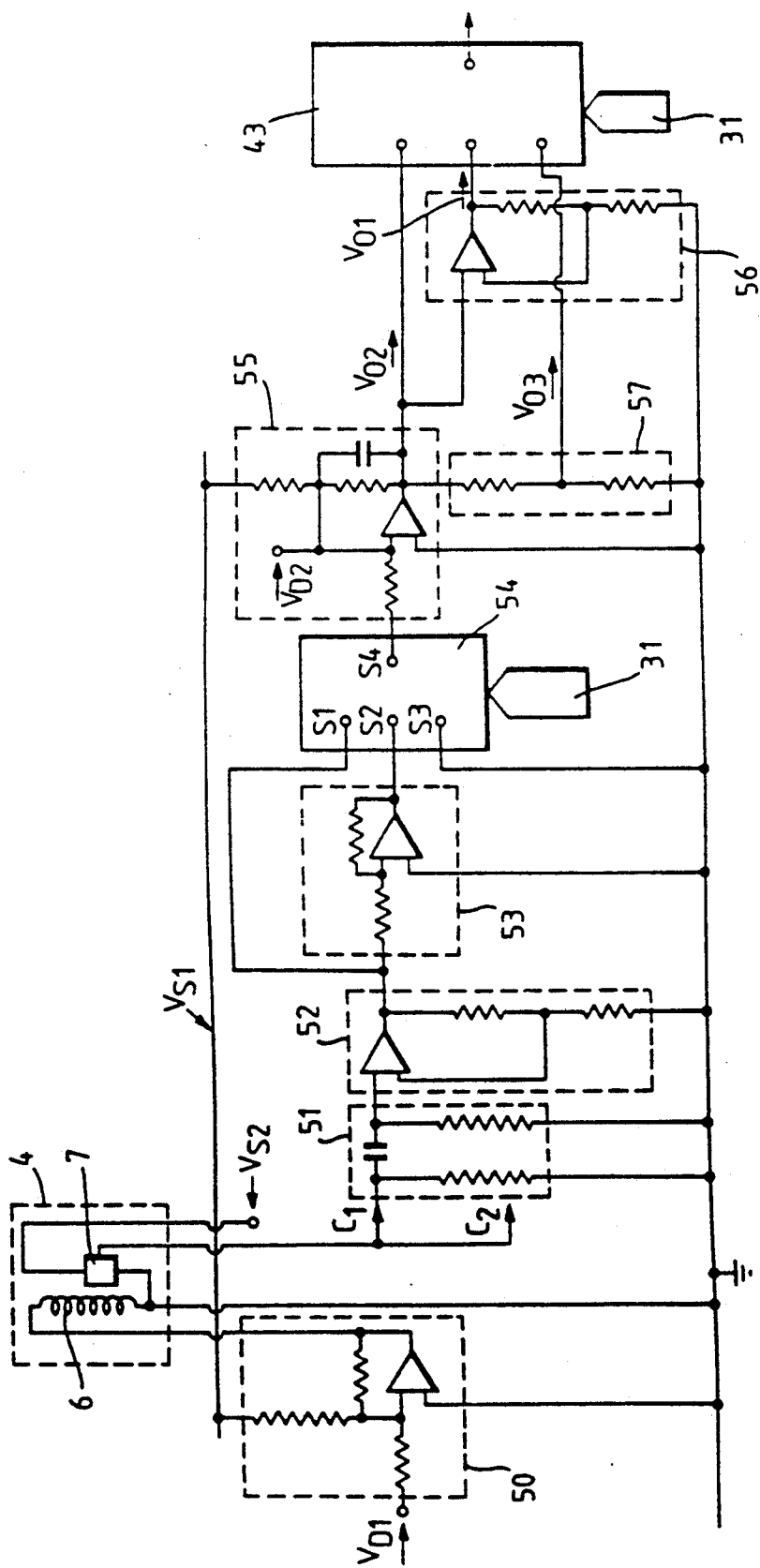
FIG. 5 is a circuit diagram depicting the analogue circuits.
Figure 6:
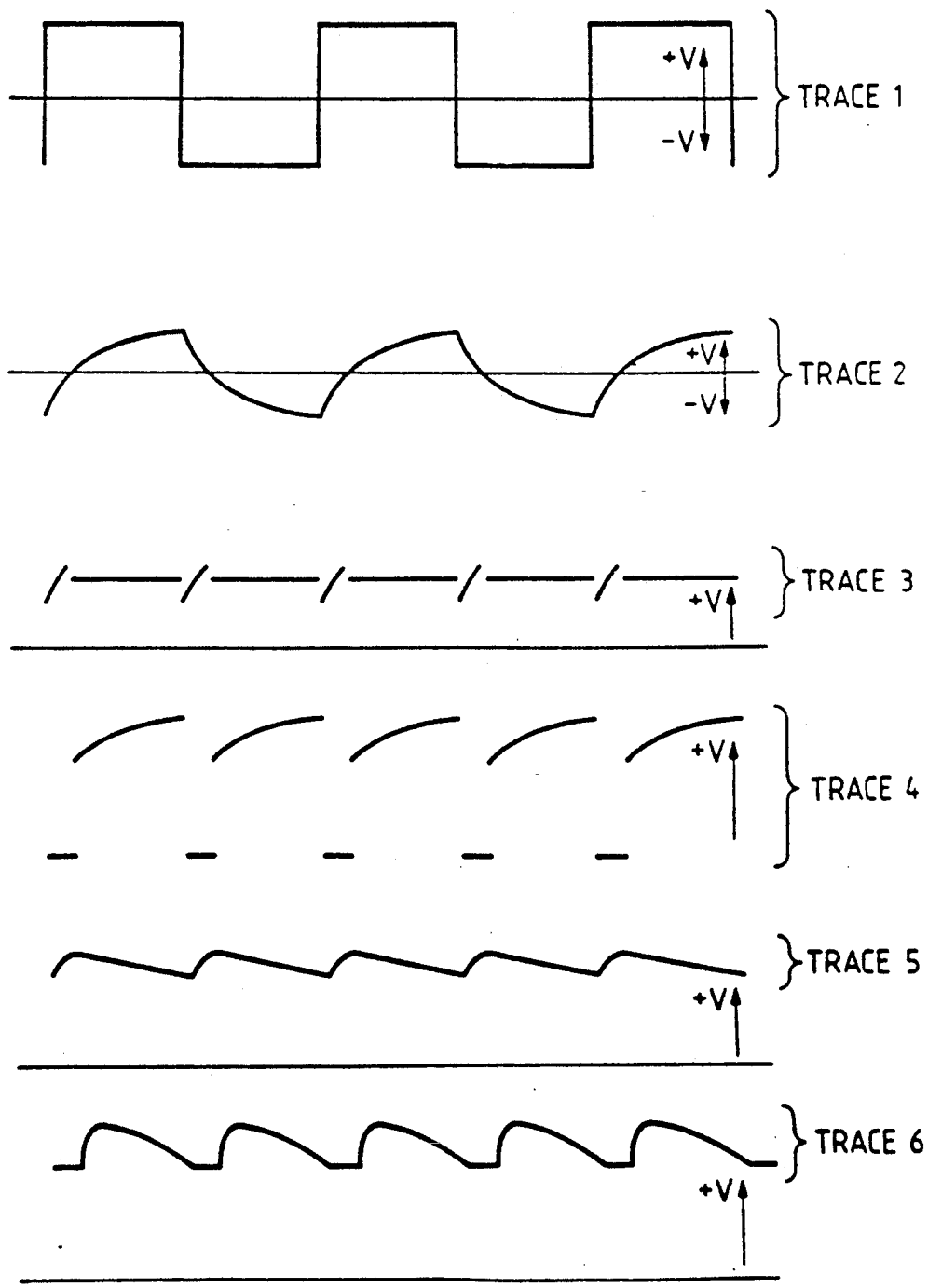
FIG. 6 is a waveform diagram illustrating the signal form at various points in the analogue circuit.
Figure 7:
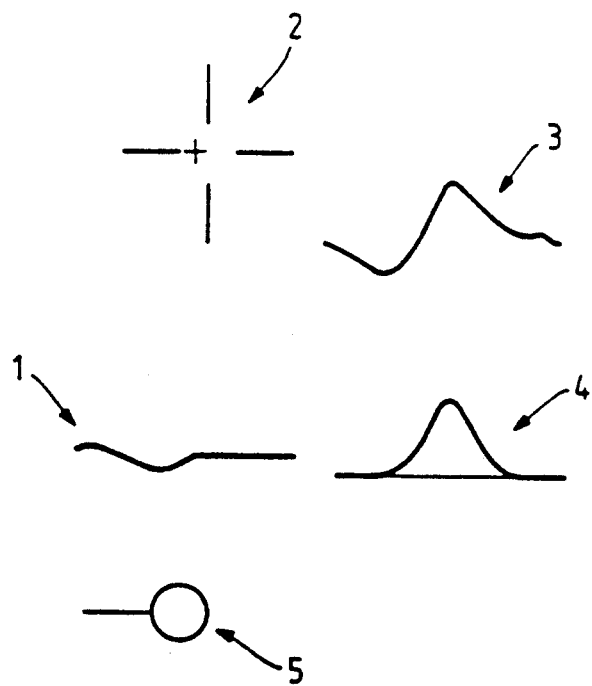
FIG. 7 is an illustration of a typical output display.

The next stage of this description is given with reference to FIGS. 5, 6 and 7. FIG. 5 depicts the elements of the analogue circuit board 38 relating to one channel of the equipment and the interconnections with the electromagnetic unit 4. FIG. 6 illustrates signal waveforms at various locations on board 38. Note that in this Figure the waveforms are shown to a common time scale but not to a common amplitude scale. FIG. 7 shows a typical VDU display.

The excitation voltage applied to coil 6 of the electromagnetic unit 3 is a square wave alternating between +5 v and −5 v levels—see trace 1 of FIG. 6. This is produced by square wave generator 50 triggered by the output of DAC39. An alternation of level is established upon receipt at DAC39 of every tenth interrupt so that these alternations take place at 3 millisecond intervals and in synchronism with other system activities. Energy is transferred to the test structure from the excitation coil 6 by induction whenever there is a change in the magnetic flux penetrating its material. Each alternation of the square wave at trace 1 creates a step change in that magnetic flux and in consequence imposes a sharp electromagnetic impulse to the test structure which propagates outwards and downwards with a finite velocity. The velocity of propagation for a 1 kHz electromagnetic wave in aluminium is around 30 m/s. In the absence of some discontinuity within the material the pulses will be dispersed within the material though in doing so they will give rise to eddy currents which will modify the field at the surface of the test structure and hence effect the signal of magnetic detector 7. The step impulses given to the test structure may be considered as comprising a series of components of different frequencies and the lower frequency components will penetrate further within the test structure than the others. Any discontinuity within the test structure, such as a crack or a boundary surface, which is within the footprint of the electromagnetic unit 4 will cause some reflection of the incident magnetic pulse which will modify to some degree the surface field measured by the magnetic detector 7 when it passes over the appropriate region or the surface. Trace 2 of FIG. 6 shows the general form of the magnetic detector output. The waveform comprises an alternating signal in synchronism with the excitation square wave. Each alternation is of generally exponential form being dominated by two principle component: the square wave primary field generated by the excitation current, and an opposing secondary field generated by the energy transferred to the workpiece through electromagnetic induction. By examining the variation of this signal as the electromagnetic unit 4 rotates information may be obtained regarding the positioning of the probe 10 with respect to the fastener (to aid centering) and regarding the presence and position of cracks etc within the test structure. Because the applied electromagnetic impulses travel through the test structure with finite velocity reflections from various depths will arrive at the surface at differing times. The signal produced by the magnetic detector 7 is chopped into various time slices synchronised against the square wave excitation signal (one slice per channel of the analogue circuit board 38) so as to aid in the discrimination of flaws from other field modifying features of the workpiece and to yield information regarding the depth of detecting flaws.

Electrical connection to the electromagnetic unit 4 are made through the connector 18 and slip rings 16. A constant dc level $Vs_2$ is provided as supply to the Hall effect magnetic detector 7. The signal from magnetic detector 7 is directed to each of the separate channels in the analogue circuit board. There can be any number of these channels according to the degree of depth discrimination required of the equipment. Two channels are indicated in FIG. 4 but only one, designated C1, is detailed as the channels are identical in circuitry. The channels differ only in respect of their individual switching stratgegies and consequential analysis bands.

The input stage to the channel comprises a high pass filter 51 (cut off frequency around 30 Hz) which serves to remove any variation in signal level around the scan caused by pick up of the earth's magnetic field. The filtered signal is amplified by amplifier 52 and this amplified signal is provided to a terminal S1 of a switching integrated circuit (IC) 54. A parallel leg passes from the filter output to terminal S2 of the switching IC through a unity gain inverting amplifier 53. A terminal S3 of the switching IC is earthed. The switching IC is a CMOS latched analogue multiplexer device and is operated by the microprocessor 30 according to a predetermined switching strategy for that channel, so as to connect as required any one of terminals S1, S2 and S3 to an output terminal S4. All changes in switch positions are made upon an interrupt and within each channel are made at predetermined points in synchronism with the square wave excitation signal. For all channels there is an alternation between connections S1/S4 and S2/S4 which ensures that the signal at the switch output is a rectified version of the input signal. For each channel there is within the period of each half wave a band in which the incoming signal is suppressed by breaking the S1/S4 or S2/S4 connection and making the S3/S4 connection. This band is called hereafter the rejected band and the remainder is termed the gated band. One channel, say channel C1, is controlled so that the front portion of each half wave is gated—typically that one tenth portion between the originating and first subsequent interrupt—with the remainder rejected. The other channel or channels are controlled so as to reject the front portion of each half wave and gate any respective portion (in tenths) or the whole of the remainder. Traces 3 and 4 of FIG. 6 show the signal waveform at S4 in two different channels. Trace 3 depicts the front gated signal in channel C1 and trace 4 depicts the signal in another channel, say C2, where the front one tenth is rejected and the remaining nine tenths gated. The variation in level from half wave to half wave within trace 4 is dominated by near-surface phenomenon because the gated time interval does not provide sufficient time for reception of reflected impulse signals of deeper origin. This provides immunity from crack effects within this channel and a signal which may be processed to give a good indication of the probes' misalignment. The variation in level from half wave to half wave in front rejected channels is relatively immune to surface phenomenon and is not cluttered when surface features such as inscriptions pips or dimples are present on the fastener head. Further reduction in width of the gated portion from within that behind the rejected front portion provides a narrower pass band in terms of pulse/reflection transit time and so provides greater discrimination for crack depth estimation.

The gated signal within each channel is passed to the input of the first order low pass filter 55. The signal at this stage is centered upon a frequency of 160 Hz with a possible information bandwidth of ±40 Hz. Filtering by filter 55 improves the signal to noise ratio considerably by removing a significant proportion of the wide band noise originating from the Hall effect magnetic detector 7. At the input to filter 55 the incoming signal is balanced against a generated dc reference level $V_{D2}$ to reduce the dc level. This permits the signal to be amplified without swamping the circuitry with dc level and enables an improved dynamic range to be achieved. Reference voltage $V_{D2}$ is produced by DAC40 under control of the microprocessor 30 and the value of $V_{D2}$ is updated three times per motor revolution so as to maintain the output of the filter within reasonable limits. Filter 55 integrates the gated signal for sampling with a view to detecting changes in level from half wave to half wave. The equipment is configured to provide three different signal gain settings. An intermediate gain level is provided by the unmodified output of filter 55, indicated as $V_{O2}$. An amplifier 56 provides a high gain output, indicated as $V_{O1}$. A voltage divider 57 provides a low gain output indicated as $V_{O3}$. Traces 5 and 6 provided typical signal waveforms at the output of filter 55 for a front-gated channel (of trace 3) and a rear-gated channel (of trace 4) respectively. It will be seen that this output signal comprises a dc level with a significant ripple superimposed thereon which is synchronous with the excitation square wave (trace 1). The effects of these ripples are overcome by taking for each half wave period a series of samples at time intervals which are synchronised from half wave to half wave, and averaging these. The three output signals ($V_{O1}$-$V_{O3}$) from each channel are passed to respective input terminals of an analogue multiplexor 42 which is driven from the bus 31. At the occurrence of each interrupt the multiplexer 42 performs a sampling sequence. The analogue signal from each channel (at a level $V_{O1}$-$V_{O3}$ determined by the microprocessor 30) is passed in turn to an ADC 43 for a predetermined sampling period by means of a sequence of switching operations within the multiplexer 42. Thus for each interrupt a corresponding data value is generated for each channel. There are ten data values per channel for each 3 milliseconds between alternations of the excitation square wave and eighty alternations per revolution of the electromagnetic unit 4. Within the digital circuits of the equipment the ten data values for each period between consecutive alternations of the excitation square wave are summed and averaged then this mean value is averaged with the next following to produce a mean value for the two. This yields 80 processed data values per revolution of the electromagnetic unit 4 per channel of the equipment and each corresponds to a measurement obtained at a respective angular location in the rotation. These 80 processed data values per revolution are used to generate a visual display upon VDU 37. FIG. 7 depicts a typical display for a two channel equipment. Display 1 shows the 80 processed data values for the front end gated channel C1 of the equipment. Display 2 relates the probe position to the centre of the fastener head and this display is used to aid manual centering of the probe 10. Display 2 is generated by the microprocessor 30 from the data used to generate display 1, by determining the phase of the misalignment sinusoid with respect to the datum pulse generated by magnetic pick-up 19 and by determining its amplitude also. Display 3 shows the 80 processed data values for channel C2 which gates all but the first tenth of each half wave. Display 3 shows a significant rotational frequency sinusoidal component which follows from the misalignment. This is reduced but not eliminated by iterative manual centering. The residual element is removed by further data processing to give an enhanced crack signal display shown as display 4. The technique used adds the first processed data value (derived as described above) to the fortieth, the second to the forty first and so on through the 80 such values. The variation of these summed values over the rotation is shorn of any fundamental frequency sinusoid but at the expense of generating a ghost signal of the crack. The true crack signal is distinguished from the ghost signal by reference to the second derivatives of the presumed values and the ghost signal is suppressed to give display 4. Display 5 which relates the crack position in azimuth to the probe orientation is derived by comparison of the phase of any crack signal indicated in display 4 with respect to the datum pulse of the magnetic pick-up 19.

Whilst the equipment as described and illustrated incorporates a circular platform coil and core which is rotated with the magnetic detector in the probe unit no rotation of such a core is required in order to generate a symmetric field with a circular footprint. An alternative probe might incorporate a sector shaped core or a linear core swept in rotation about the centre of the probe in unison with the magnetic detector. Other forms of drive motor and probe construction may be adopted as may be other means to provide signal processing in the way described. The gated signal could be passed to a switching integrator rather an integrator in the form of a low pass filter. These any many other variations to the invention as described will be apparent to those skilled in the art and are within the scope of the appended claims.

I claim:

1. A method of non-destructively testing electrically conductive articles for the presence of flaws using eddy currents, the method comprising the steps of:
   applying a repetitive square wave excitation signal to a coil placed upon an article to be tested, said coil providing a circular footprint of magnetic field;
   moving a magnetic field detector along a circular scan path on the surface of the article within the footprint of the magnetic field, said movement synchronized with said excitation signal, said detector being responsive to low frequency variations of magnetic field;
   examining the field signal sensed by said detector for variations in echo component of the field signal consequent upon the change in position of the detector on the scan path;
   gating the detected field signal at set time intervals synchronised to the excitation signal to define at least one series of time bands, each time band of a series falling within a respective half-wave portion of the excitation signal, such that each series of time bands registers echoes of the excitation signal from a depth zone within the article under test for which the aggregate signal transit times to and from the depth zone fall within the gated interval; and measuring the signal level for each time band of each series and comparing the measured signal levels within a series to identify any change in level from a predominant background level, wherein a change in measured signal level is indicative of an echo from a discontinuity in the material of the article under test in the depth zone corresponding to the gated interval, the azimuth position of said discontinuity being indicated by the temporal position of the change in level within the respective series of time bands.

2. A method as claimed in claim 1 wherein said gating step excludes that portion of the field signal generated by the first temporal portion of each half wave of the excitation signal and thereby eliminate echoes of the excitation signal from the surface of the article under test.

3. A method as claimed in claim 1 wherein said signal level measuring step includes measuring at set intervals synchronised to the excitation signal and producing a plurality of measurements for each time band, averaging said plurality of measurements for each time band to give a mean value for respective individual time bands such that comparison between measured levels within a respective series of time bands is immune to clutter having the periodicity of the excitation signal.

4. A method as claimed in claim 1 wherein a fastener, having a center, is tested and said gating step includes timing the gating of the detected field signal to define a series of time bands which consist solely of that portion of the field signal generated by the first temporal portion of each half wave of the excitation signal to exclude echoes of the excitation signal from beneath the surface of the article and comparing the signal level of each time band with other signal levels in the series to determine the position of the peak signal level within this series and to determine its magnitude, thereby indicating any misalignment between the center of said circular scan path and a center of said fastener.

5. Apparatus for non-destructively testing electrically conductive articles for the presence of flaws using eddy currents, the apparatus comprising:
  a probe unit locatable on the article under test, said probe unit comprising:
    an excitation coil;
    a magnetic field detector for detecting incoming field signals, said detector being responsive to low frequency variations of magnetic field; and
    rotational drive means for driving the detector along a circular scan path overlying and adjacent to the article under test;
  an excitation signal generator for energising the excitation coil with a repetitive square wave excitation signal in synchronism with the motion of the detector along said scan path;
  a field signal processor for processing the output of detector, said processor having at least one channel, said at least one channel comprising:
    a switching device for gating the incoming field signal from the detector at intervals in synchronism with the excitation signal so as to pass a series of time bands of the field signal, there being one time band for each half-wave portion of the excitation signal; and
    an integration circuit for integrating the field signal level within each passed time band of the series;
  measurement means for measuring at each of said at least one channel, the integrated signal level for each time band in a respective series; and
  means for comparing the integrated signal levels of a series and for indicating variations from a predominant background level.

6. Apparatus as claimed in claim 5 wherein said detector is a Hall effect device.

7. Apparatus as claimed in claim 5 wherein the field signal processor has at least two channels, each of said at least two channels including means for gating a different series of respective time bands of the field signal.

8. Apparatus as claimed in claim 7 wherein said at least two channels comprise a means for providing a series of time bands of field signal which consists solely of that portion of the field signal generated by a first temporal portion of each half-wave of the excitation signal, and wherein at least one other channel is arranged to provide a series of time bands of field signal comprising the field signal generated by a remaining temporal portion of each half-wave of the excitation signal.

9. Apparatus as claimed in claim 7 further including a computer having a processor and a memory unit wherein the computer comprises a means for maintaining synchronism between the excitation signal generator and coordinated operations of the switching device in each channel of the field signal processor.

10. Apparatus as claimed in claim 9 in which said computer includes means for causing said measurement means to sample the integrated signal level of each time band of field signal in a respective series at least once for each time band and at intervals which are in synchronism with the excitation signal, for generating a value of signal level for each time band in a respective series for comparison with the generated signal levels for other time bands in the same series.

11. Apparatus as claimed in claim 10 in which said electrically conductive articles include a fastener at a fastener position, said indicating means comprises a visual display unit, wherein at least in a centering mode of the apparatus, one channel of the field signal processor comprises a means for providing a series of time bands of field signal consisting solely of that portion of the field signal generated by the first temporal portion of each half-wave of the excitation signal, wherein said computer includes means for measuring the integrated signal level of each time band in the series, for comparing these levels and, by locating the position of the peak level in the series and its magnitude, for providing on the visual display unit an indication of the azimuth angle of the alignment error or correction angle, and an indication of the alignment error distance.

12. A method as claimed in claim 2 wherein said signal level measuring step includes measuring at set intervals synchronised to the excitation signal and producing a plurality of measurements for each time band, averaging said plurality of measurements for each time band to give a mean value for respective individual time bands such that comparison between measured levels within a respective series of time bands is immune to clutter having the periodicity of the excitation signal.

* * * * *